United States Patent
Descheres et al.

(10) Patent No.: US 6,444,770 B1
(45) Date of Patent: Sep. 3, 2002

(54) ACRYLAMIDE AND TRIALKYLAMMONIUM SALT COPOLYMER, METHOD FOR OBTAINING SAME AND COATED TEXTILE

(75) Inventors: Isabelle Descheres; Gilbert Boulon, both of Lyons (FR)

(73) Assignee: Atofina, Paris (FR)

( * ) Notice: Subject to any disclaimer, the term of this patent is extended or adjusted under 35 U.S.C. 154(b) by 0 days.

(21) Appl. No.: 09/622,168

(22) PCT Filed: Jul. 22, 1999

(86) PCT No.: PCT/FR99/01802

§ 371 (c)(1),
(2), (4) Date: Aug. 14, 2000

(87) PCT Pub. No.: WO00/05281

PCT Pub. Date: Feb. 3, 2000

(30) Foreign Application Priority Data

Jul. 23, 1998 (FR) .............................. 98 09584

(51) Int. Cl.⁷ .............................. C08F 218/00
(52) U.S. Cl. .............. 526/307.7; 526/303.1; 526/307.2; 526/307.4
(58) Field of Search .......... 526/303.1, 307.2, 526/307.4, 307.7

(56) References Cited

U.S. PATENT DOCUMENTS 4,058,491 A * 11/1977 Steckler .................... 260/2.2 R
4,429,096 A * 1/1984 Schaefer .................... 526/287
5,614,602 A * 3/1997 Connors et al. ......... 526/307.3

FOREIGN PATENT DOCUMENTS

FR 2695800 * 3/1994

* cited by examiner

*Primary Examiner*—Helen L. Pezzuto
(74) *Attorney, Agent, or Firm*—Hunton & Williams

(57) ABSTRACT

A copolymer of acrylamide or of an acrylamide derivative and of trialkylammonium salts which is a radical polymerization product, in the presence of an initiator, of at least a first monomer chosen from acrylamide and its derivatives of formula

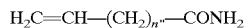

$$H_2C=CH-(CH_2)_{n''}-CONH_2$$

in which n" is an integer which can vary from 1 to 5, and of a second monomer chosen from trialkylammonium salts corresponding to the following formula (I)

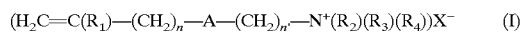

$$(H_2C=C(R_1)-(CH_2)_n-A-(CH_2)_{n'}-N^+(R_2)(R_3)(R_4))X^- \quad (I)$$

in which, $R_1$ represents H or an alkyl group having from 1 to 3 carbon atoms, $R_2$, $R_3$ and $R_4$, which are identical or different, each represents an alkyl group having from 1 to 3 carbon atoms, n and n' each represents, independently of one another, a non-zero integer at most equal to 15, A represents a divalent carboxyl or amide functional group, and $X^-$ represents a counterion.

18 Claims, No Drawings

ACRYLAMIDE AND TRIALKYLAMMONIUM SALT COPOLYMER, METHOD FOR OBTAINING SAME AND COATED TEXTILE

BACKGROUND OF THE INVENTION (i) Field of the Invention

The present invention relates to a copolymer of acrylamide or acrylamide derivative and of trialkylammonium salts which exhibits a biocidal nature and is intended in particular for the coating of substrates.

In the following description, the invention is more particularly set out with reference to a copolymer for the impregnation of a textile substrate, but, of course, it should not be regarded as being limited thereto, it being possible for the copolymer of the invention to be applied to other substrates, such as leather, wood or plastic substrates.

The term "biocidal" is understood to mean the property which consists in destroying a microorganism, such as fungi, yeasts or bacteria. More specifically, the copolymer which is the subject-matter of the invention exhibits, and confers on the substrate to which it is applied, a contact biocidal nature, which means that it directly brings about the death of the microorganisms by simple contact.

The present invention is mainly of advantage in the medical field, where the need to have available means for protecting against pathogenicagents is ceaselessly increasing.

(ii) Description of the Related Art

The properties required for a textile for medical use are, first, a biocidal effect and good absorption of liquids.

A biocidal or antiseptic compound corresponding to the following formula:

in which, $R_1$ represents H or $CH_3$, $R_2$, $R_3$ and $R_4$ each represent an alkyl group such that the total number of carbon atoms of $R_2$, $R_3$ and $R_4$ varies from 6 to 15, n varies from 1 to 3, B represents $CH_2$, a carboxyl functional group or an amide functional group, and $X_-$ represents a counterion, is known according to the document FR-A-2,695,800.

The compound disclosed is used for the preparation of biocidal fabric cotton textile under conditions of grafting the compound by radical activation under the effect of ionizing radiation, such as γ radiation.

The manufacture on an industrial scale of a biocidal textile as disclosed according to FR-A-2, 695, 800, and more particularly the stage of grafting the compound to the substrate, represents a very heavy technological investment and, furthermore, requires a workforce necessarily trained in nuclear techniques, due to the harmful effects of such radiation.

SUMMARY OF THE INVENTION

The Applicant Company has discovered a biocidal product which makes it possible to solve the problem posed by known biocidal compounds by introducing a product which can be attached to a substrate by simple impregnation. In particular, when. the substrate is textile, the attachment of the product can be carried out by standard techniques of this industry, in particular padding.

The product of the invention consists of a copolymer which can be obtained by radical copolymerization, in the presence of an initiator, of at least a first monomer chosen from acrylamide and its derivatives of formula

in which n" is an integer which can vary from 1 to 5 and advantageously from 1 to 3;

and of a second monomer chosen from trialkylammonium salts corresponding to the following formula (I)

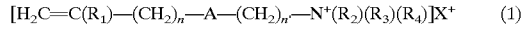

in which, $R_1$ represents H or an alkyl group having from 1 to 3 carbon atoms, $R_2$, $R_3$ and $R_4$, which are identical or different, each represent an alkyl group having from 1 to 3 carbon atoms, n and n' each represent, independently of one another, a non-zero integer at most equal to 15, A represents a divalent carboxyl or amide functional group, and $X^-$ represents a counterion.

Preferably, the first monomer is acrylamide or else the second monomer corresponds to the abovedescribed formula (I) in which n varies from 7 to 9, n' varies from 2 to 4 and $X^-$ represents $Cl^-$, $F^-$ or an alkyl sulphate ion.

The second monomer advantageously corresponds to the abovedescribed formula (I) in which $R_1$ represents H; $R_2$, $R_3$ and $R_4$ are identical and each represent the methyl group; n is equal to 8 and n' is equal to 3; A represents the amide functional group; and $X^-$ represents the methyl sulphate ion.

As will be illustrated in the examples at the end of the description, a particularly advantageous copolymer according to the invention is that which can result from the copolymerization between the preferred first monomer and the preferred second monomer identified above.

More advantageously still, the weight-average molecular weight (Mw) of the copolymers is between 6000 and 10,000.

According to an alternative form of the invention, a copolymer can consist of a terpolymer which can be obtained by radical copolymerization at least of the first monomer, of the second monomer and, in addition, of a third monomer chosen from acrylic acid and vinyl esters. Mention may be made, as examples of such esters, of vinyl acetate, vinyl propionate and vinyl butyrate.

Another subject-matter of the invention is a process for preparing a copolymer defined above. It comprises the stages consisting in reacting at least a first monomer, a second monomer and optionally a third monomer, as have been defined above, in a solvent at the reflux temperature, in the presence of an initiator.

Preferably, the first monomer is acrylamide and/or the second monomer corresponds to the formula (I) in which n varies from 7 to 9, n' varies from 2 to 4 and $X^-$ represents $Cl^-$, $F^-$ or an alkyl sulphate ion.

The second monomer advantageously corresponds to the formula (I) in which $R_1$ represents H; $R_2$, $R_3$ and $R_4$ are identical and each represent the methyl group; n is equal to 8 and n' is equal to 3; A-represents the amide functional group; and $X^-$ represents the methyl sulphate ion. If appropriate, the third monomer is acrylic acid.

Moreover, the process of the invention exhibits the following preferred characteristics, considered alone or in combination:

the molar concentration of the second monomer is at least equal to 20% with respect to the final molar concentration of the first and second monomers and of the third monomer, if necessary; this concentration is advantageously at least equal to 25% and at most equal to 40%;

the solvent in which the monomers are reacted is a water/ethanol mixture in a molar ratio preferably varying from 25/75 to 50/50;

the initiator is chosen from 2,2'-azobis(2-amidinopropane) hydrochloride and potassium persulphate;

the first, second and optionally third monomers are reacted under a nitrogen flow.

Another subject-matter of the invention is a textile coated with a copolymer of the invention. This textile is preferably chosen from cotton fabrics and polyester nonfabrics, which are the most frequently employed textiles, in particular in the medical field.

The invention also relates to the use of a copolymer defined above for preparing a textile which is biocidal by contact.

DETAILED DESCRIPTION OF PREFERRED EMBODIMENTS

The characteristics and advantages of the subject-matters of the invention are demonstrated in the following Examples 1 to 4.

EXAMPLE 1

Preparation of a Preferred Copolymer According to the Invention

1. Products Involved

Monomers:

First monomer: acrylamide

Second monomer: trimethyl (undecylamidopropyl) ammonium methyl sulphate (Noramium® MU 50; Elf Atochem S.A.) of formula:

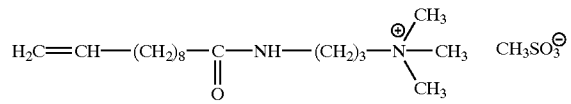

Third monomer: acrylic acid

Initiator: 2,2'-azobis(2-amidinopropane) hydrochloride (V50®; Wako) or potassium persulphate Solvent: water/methanol mixture.

2. Principle

The copolymerization is carried out under pad-batch conditions, that is to say by simultaneous introduction in a single step of the monomers into the reactor, under a nitrogen flow (in order to remove the dissolved oxygen, which is a polymerization inhibitor) and at 70° C. (reflux temperature of the methanol).

The formulations are prepared for a volume of solution of 1 liter (synthesis on a laboratory scale) and 100 liters (synthesis on an industrial scale).

3. Equipment

Synthesis on a laboratory scale is carried out in a two-liter reactor comprising a jacket, which jacket is connected to a thermostatically-controlled bath, and equipped with a reflux condenser terminated by a bubbler, with a mechanical stirrer indicating the rotational speed and with an inlet for the introduction of the various products.

Use is made, for synthesis on an industrial scale, of a 300-liter reactor equipped with similar facilities and with a nitrogen inlet.

4. Synthesis of the Copolymer

Synthesis on a laboratory scale

Various copolymers are prepared: copolymers based on acrylamide and on Noramium® MU 50 and terpolymers based on acrylamide, on Noramium® MU 50 and on acrylic acid, while varying, for each synthesis, the following parameters: proportions of the various monomers (Noramium® MU 50/acrylamide/acrylic acid, abbreviated to Nor/Acry/AcryAc), overall monomer concentration, and methanol concentration.

The concentration of initiator V50® is constant (1 g/l).

The parameters chosen for the syntheses and the results are collated in Table 1.

Synthesis on an industrial scale

The two copolymer solutions prepared correspond to the above copolymer solutions 19 and 26. They are obtained under the conditions of Table 1, with the exception of the fact that the initiator employed is potassium persulphate. The copolymers obtained (19' and 26', respectively) are identical.

5. Characterization of the Copolymer

The copolymer obtained is characterized by its final appearance (homogeneous solution, heterogeneous solution or gel), by the number-average molecular mass (Mn) and the weight-average molecular mass (Mw), and by the polydispersity index (PI=Mw/Mn), determined by gel permeation chromatography. These parameters appear in Table 1.

TABLE 1

| Water/Methanol Solvent Ratio | Monomers | | Physical | | | | |
|---|---|---|---|---|---|---|---|
| | Nor/Acry/AcryAc Ratio | Concentration of (%) | No. | appearance of the product | Mn ± 5% | Mw ± 5% | PI |
| 50/50 | 10/90/0 | 10 | 14 | Solution | 29,000 | 33,700 | 1.2 |
| | 25/75/0 | 10 | 19 | Solution | 6500 | 13,500 | 2.1 |
| | 50/50/0 | 10 | 16 | Solution | 1000 | 5800 | 5.7 |
| | 10/88/2 | 10 | 24 | Solution | 18,000 | 30,700 | 1.7 |
| | 10/88/2 | 25 | 23 | Gel | 20,000 | 31,500 | 1.6 |
| | 25/73/2 | 10 | 27 | Solution | 13,000 | 22,600 | 1.8 |
| | 25/65/10 | 10 | 26 | Solution | 9000 | 17,200 | 1.9 |
| 75/25 | 10/88/2 | 25 | 22 | Gel | 16,700 | 28,200 | 1.7 |
| | 25/73/2 | 10 | 25 | Solution | 11,700 | 21,200 | 1.8 |
| 100/0 | 10/88/2 | 10 | 20 | Solution | 7600 | 17,100 | 2.2 |
| | 10/88/2 | 25 | 21 | Gel | 17,000 | 27,000 | 1.6 |

EXAMPLE 2

Bactericidal Power of the Copolymers

1. Principle

The copolymer solution is brought into contact with a known population of *Pseudomonas aeruginosa* ATC 9027 or *Staphylococcus aureus* ATCC 6538 which has been grown for approximately 12 hours in an oven at 30° C. in an initially sterile nutrient medium.

If $N_0$ (bacteria/cm$^3$) is the initial bacterial population and $N_t$ (bacteria/cm$^3$) is the population at time t, the bacterial power is measured by calculating $\log(N_t/N_0)$.

The following effect is attributed to the values of $\log(N_t/N_0)$:

| $\log(N_t/N_0)$ | Effect |
| --- | --- |
| Zero | bacteriostatic |
| Negative | bactericidal |
| Positive | no |

2. Counting of the Bacteria

Use is made of the dilution method known as "Microbiological tests" described in "United States Pharmacopeia XIX".

The bacteria are counted according to the method known under the name "Most Probable Total Count by Multiple-tube Method".

3. Results

The bactericidal power of the copolymer solutions 14, 16 and 19, calculated according to a contact time varying from 1 to 24 hours, is given in Table 2.

The concentration as Noramiuma® MU 50 (Nor) equivalent of each copolymer solution is expressed in mol/l.

TABLE 2

| Co-polymer Solution No. | T (hours) | *Pseudomonas aeruginosa* Population N (bacteria/ml) | $\log(N_t/N_0)$ | *Staphylococcus aureus* Population N (bacteria/ml) | $\log(N_t/N_0)$ |
| --- | --- | --- | --- | --- | --- |
| 14 | 0 | $2.5 \times 10^7$ | — | $4.5 \times 10^6$ | — |
| (Nor = | 1 | $9 \times 10^3$ | −3.44 | ND | ND |
| 0.10) | 4 | $5 \times 10^3$ | −3.70 | $4.5 \times 10^2$ | −4.00 |
|  | 7 | $9 \times 10^2$ | −4.44 | ND | ND |
|  | 24 | $3 \times 10^2$ | −4.92 | $2.5 \times 10^2$ | −4.25 |
| 19 | 0 | $2.5 \times 10^7$ | — | $4.5 \times 10^6$ | — |
| (Nor = | 1 | $5 \times 10^3$ | −3.70 | ND | ND |
| 0.17) | 4 | $5 \times 10^2$ | −4.44 | $3 \times 10^2$ | −4.17 |
|  | 7 | $3 \times 10^2$ | −4.92 | ND | ND |
|  | 24 | $3 \times 10^2$ | −4.92 | $2.5 \times 10^2$ | −4.25 |
| 16 | 0 | $2.5 \times 10^7$ | — | $4.5 \times 10^6$ | — |
| (Nor = | 1 | $9 \times 10^2$ | −4.44 | ND | ND |
| 0.20) | 4 | $3 \times 10^2$ | −4.92 | $2.5 \times 10^2$ | −4.25 |
|  | 7 | $3 \times 10^2$ | −4.92 | ND | ND |
|  | 24 | $3 \times 10^2$ | −4.92 | $0.9 \times 10^2$ | −4.69 |

ND = not determined

It is observed that the biocidal activity is very high for all the copolymer solutions, from the first hour.

When the Noramium® MU 50 concentration in the solution increases, the biocidal activity of the polymer increases.

EXAMPLE 3

Preparation of a Textile with a Biocidal Nature

1. Textile

Use was made of a cotton fabric and of a 70 g/m$^2$ polyester nonfabric.

2. Impregnation

The trials are carried out with the copolymers 14, 16, 19, 20, 24, 25 and 26.

For the impregnation, the following conditions are:

Horizontal padding mangle from Laboratoire Werner Mathis,
  rolls: hardness of the rubber 70° Shore, width 350 mm, diameter 110 mm,
  pressure between the rolls: 100%, i.e. 40–45 kg/cm,
  depth of immersion in the bath: 40 mm, Thermosetting treatment (vaporizing of water), Drying on a stenter at 50° C., Direct impregnation, according to which the copolymer solution is placed between the rolls of the padding mangle, One or two passes in the padding mangle.

The various trials are compared according to:

the level of the loading, the quality of the feel, with the following key: -- means a very poor feel (pronounced "cardboard" effect), − means a poor feel (stiff textile), + means an average feel and ++ means a pleasant feel (virtually identical to that of the untreated textile).

The results are collated in Table 3.

TABLE 3

| Type of Textile | Copolymer Solution No. | Number Passes Padding mangle | Level of loading on a dry basis (%) | Quality of the feel |
| --- | --- | --- | --- | --- |
| Cotton fabric | 14 | 1 | 11 | − |
|  |  | 2 | 11 | − |
|  | 19 | 1 | 9.7 | + |
|  |  | 2 | 8.8 | + |
|  | 16 | 1 | 7.6 | + |
|  |  | 2 | 6.9 | + |
|  | 24 | 1 | 12.4 | − |
|  | 27 | 1 | 10.8 | + |
|  | 26 | 1 | 12.2 | + |
|  | 25 | 1 | 10.4 | + |
|  | 20 | 1 | 10.7 | − |
| Nonfabric | 14 | 1 | 17.5 | -- |
|  |  | 2 | 19.4 | − |
|  | 19 | 1 | 15 | + |
|  |  | 2 | 16.7 | + |
|  | 16 | 1 | 55.6 | + |
|  |  | 2 | 12.8 | + |
|  | 24 | 1 | 20 | − |
|  | 27 | 1 | 14.2 | + |
|  | 26 | 1 | 19.5 | + |
|  | 25 | 1 | 1.3 | + |
|  | 20 | 1 | 17.8 | − |

As regards the level the level of loading, that is to say the amount of polymer attached to the substrate, the results are relatively close, whatever the silutions used (with or without acrylic acid).

The results of the textile application are entirely acceptable.

It should be noted that trials carried out on a cotton fabric and on a nonfabric with all the abovementioned copolymer solutions gave similar results in terms of quality of the feel.

EXAMPLE 4

Bactericidal Power of an Impregnated Textile

1. Principle

The principle of this test, disclosed in the document FR-A-2,695,800, is restated hereinbelow.

Samples with an identical size (discs with a diameter of 34 mm) of each of the substrates are introduced into sterile flasks (diameter substantially identical to the disc), so as to completely cover the lower surface.

A suspension of *Pseudomonas aeruginosa* ATCC 9027 is prepared (0.4 ml in nutrient medium) and introduced into an oven at 30° C. for a few hours.

The following are prepared for each type of textile tested:
a sample of each trial,
two control samples (before impregnation):
one in order to determine the number of bacteria at the start ("Control 0") and the other in order to know the number of bacteria which are growing after 24 hours ("Control 24").

The samples are inoculated with:
0.2 ml of bacterial suspension for the samples of 70 g/m² nonfabric,
0.6 ml of bacterial suspension for the samples of cotton fabric.

A first counting of bacteria is carried out on the "Controls 0". The other flasks ("Controls 24"+ various trials) are introduced into an oven at 30° C. and, after 24 hours, the number of bacteria present in the medium is determined.

The bacteria are counted by the method of Example 2, paragraph 2.

2. Results

The bacteriological tests were carried out on samples of cotton fabrics (solely the fabrics after attachment) and of polyester nonfabrics which are impregnated with the copolymer solutions 14, 16, 19, 25, 26 and 27.

The results are collated in the following Table 4.

TABLE 4

| Textile | Copolymer Solution No. | Nor (mol/l) | Level of loading (%) | Time (Hours) | Control | Impregnated |
|---|---|---|---|---|---|---|
| Cotton fabric | 14 | 0.1 | 11.0 | 0 | $2.5 \times 10^4$ | ND |
| | | | | 24 | $2.5 \times 10^7$ | $3 \times 10^1$ |
| | 19 | 0.17 | 9.7 | 0 | $4.5 \times 10^3$ | ND |
| | | | | 24 | $>1 \times 10^8$ | $2.5 \times 10^1$ |
| | 16 | 0.20 | 7.6 | 0 | $4.5 \times 10^3$ | ND |
| | | | | 24 | $>1 \times 10^8$ | $4.5 \times 10^1$ |
| | 25 | — | 10.4 | 0 | $0.7 \times 10^4$ | ND |
| | | | | 24 | $>1 \times 10^9$ | $2.5 \times 10^1$ |
| | 26 | — | 12.2 | 0 | $0.7 \times 10^4$ | ND |
| | | | | 24 | $>1 \times 10^9$ | $2.5 \times 10^1$ |
| | 27 | — | 10.8 | 0 | $0.7 \times 10^4$ | ND |
| | | | | 24 | $>1 \times 10^9$ | $2.5 \times 10^1$ |
| Non-fabric | 14 | 0.1 | 17.5 | 0 | $2.5 \times 10^4$ | ND |
| | | | | 24 | $4.5 \times 10^6$ | $1.5 \times 10^2$ |
| | 19 | 0.17 | 15 | 0 | $2.5 \times 10^3$ | ND |
| | | | | 24 | $4.5 \times 10^5$ | $2.5 \times 10^1$ |
| | 16 | 0.20 | 55.6 | 0 | $2.5 \times 10^3$ | ND |
| | | | | 24 | $4.5 \times 10^5$ | $4.5 \times 10^1$ |
| | 25 | — | 1.3 | 0 | $1.5 \times 10^2$ | ND |
| | | | | 24 | $9.5 \times 10^7$ | $2.5 \times 10^1$ |
| | 26 | — | 19.5 | 0 | $1.5 \times 10^2$ | ND |
| | | | | 24 | $9.5 \times 10^7$ | $1.1 \times 10^1$ |
| | 27 | — | 14.2 | 0 | $1.5 \times 10^2$ | ND |
| | | | | 24 | $9.5 \times 10^7$ | $2.5 \times 10^1$ |

ND = Not Determined

The results obtained are excellent.

The amount of acrylic acid in the solution apparently does not influence the results.

The antimicrobial power of the nonfabric polyester substrates is generally slightly less than that of the woven cotton substrates.

What is claimed is:

1. A copolymer of acrylamide or of an acrylamide derivative and of trialkylammonium salts which is a radical polymerization product, in the presence of an initiator, of at least a first monomer chosen from acrylamide and its derivatives of formula

in which n" is an integer which can vary from 1 to 5, and of a second monomer chosen from trialkylammonium salts corresponding to the following formula (I)

in which,
$R_1$ represents H or an alkyl group having from 1 to 3 carbon atoms,
$R_2$, $R_3$ and R4, which are identical or different, each represents an alkyl group having from 1 to 3 carbon atoms,
n and n' each represents, independently of one another, a non-zero integer at most equal to 15,
A represents a divalent carboxyl or amide functional group, and
$X^-$ represents a counterion.

2. The copolymer according to claim 1, wherein n varies from 7 to 9, n' varies from 2 to 4 and $X^-$ represents $Cl^-$, $F^-$ or an alkyl sulphate ion.

3. The copolymer according to claim 2, wherein $R_1$ represents H; $R_2$, $R_3$ and $R_4$ are identical and each represents a methyl group; n is equal to 8 and n' is equal to 3; A represents the amide functional group; and $X^-$ represents a methyl sulphate ion.

4. The copolymer according to claim 2, wherein the first monomer is acrylamide.

5. The copolymer according to claim 1, which is the radical copolymerization product of at least said first monomer, said second monomer and a third monomer chosen from acrylic acid and vinyl esters.

6. A process for preparing a copolymer according to claim 1, comprising reacting
at least a first monomer chosen from acrylamide and its derivatives of formula:

in which n" is an integer which can vary from 1 to 5, and
a second monomer chosen from trialkylammonium salts corresponding to the following formula (I):

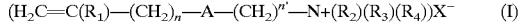

in which,
$R_1$ represents H or an alkyl group having from 1 to 3 carbon atoms,
$R_2$, $R_3$ and $R_4$, which are identical or different, each represents an alkyl group having from 1 to 3 carbon atoms,
n and n' each represents, independently of one another, a non-zero integer at most equal to 15,
A represents a divalent carboxyl or amide functional group, and
$X^-$ represents a counterion, in a solvent at the reflux temperature, in the presence of an initiator.

7. The process according to claim 6, wherein the first monomer is acrylamide and the second monomer corresponds to the formula (I) in which n varies from 7 to 9, n' varies from 2 to 4 and $X^-$ represents $Cl^-$, $F^-$ or an alkyl sulphate ion.

8. The process according to claim 6, wherein the second monomer corresponds to the formula (I) in which $R_1$ represents H; $R_2$, $R_3$ and $R_4$ are identical and each represents the methyl group; n is equal to 8 and n' is equal to 3; A represents the amide functional group; and $X^-$ represents the methyl sulphate ion.

9. The process according to claim 6, wherein the first monomer and the second monomer each has a molar concentration such that the molar concentration of the second monomer is at least equal to 20% with respect to the molar concentration of the first and second monomers.

10. The process according to claim 9, wherein the molar concentration of the second monomer is at least equal to 25% and at most equal to 40% with respect to the final molar concentration of the first and second monomers.

11. The process according to claim 6, further comprising reacting a third monomer chosen from acrylic acid and vinyl esters.

12. The process according to claim 6, wherein the solvent is a water/methanol mixture in a molar ratio varying from 25/75 to 50/50.

13. The process according to claim 6, wherein the initiator is 2,2'-azobis(2-amidinopropane) hydrochloride or potassium persulphate.

14. The process according to claim 6, further comprising reacting the first and second monomers under a nitrogen flow.

15. A textile coated with the copolymer according to claim 1.

16. The textile according to claim 15, comprising cotton fabrics or polyester nonfabrics.

17. A method for making a textile substrate which is biocidal by contact comprising coating the textile substrate with the copolymer of claim 1.

18. The process according to claim 11, further comprising reacting the first, second and third monomers under a nitrogen flow.

* * * * *